United States Patent [19]

Seidy

[11] Patent Number: 5,358,499
[45] Date of Patent: Oct. 25, 1994

[54] SANITARY NAPKIN WITH DISPOSAL MEANS

[75] Inventor: Wassim F. Seidy, Somerset, N.J.

[73] Assignee: McNeil-PPC, Inc., Milltown, N.J.

[21] Appl. No.: 181,352

[22] Filed: Jan. 13, 1994

Related U.S. Application Data

[63] Continuation of Ser. No. 16,472, Feb. 10, 1993, abandoned, which is a continuation of Ser. No. 926,550, Aug. 5, 1992, abandoned, which is a continuation of Ser. No. 827,543, Jan. 29, 1992, abandoned, which is a continuation of Ser. No. 618,012, Nov. 26, 1990, abandoned, which is a continuation of Ser. No. 489,767, Feb. 26, 1990, abandoned, which is a continuation of Ser. No. 358,539, May 30, 1989, abandoned, which is a continuation of Ser. No. 75,020, Jul. 16, 1987, abandoned.

[51] Int. Cl.$^5$ ............................................. A61F 13/16
[52] U.S. Cl. ........................................ 604/385.1; 604/387
[58] Field of Search ...................... 604/385.1, 386, 387, 604/358

[56] References Cited

U.S. PATENT DOCUMENTS

| 4,608,047 | 8/1986 | Mattingly | 604/386 |
| 4,692,162 | 9/1987 | Binker et al. | 604/385.1 |
| 4,781,712 | 11/1988 | Barabino et al. | 604/385.1 |

Primary Examiner—John D. Yasko

[57] ABSTRACT

A sanitary napkin is disclosed for providing a convenient means for disposal at minimum cost to the consumer. The napkin is capable of being rolled or folded and self-sealed for disposal and includes one or more flaps extending transversely from one end of the backing layer. The flap or flaps are wrapped around the edges of the rolled or folded napkin and sealed by adhesive means on the other end of the backing layer. Preferred adhesive means serve a dual purpose of providing for attachment to the undergarment and providing for sealing of the napkin prior to disposal.

23 Claims, 2 Drawing Sheets

SANITARY NAPKIN WITH DISPOSAL MEANS

This application is a continuation of 08/016,472 Feb. 10, 1993 now abandoned, which is a continuation of 07/926,550 Aug. 5, 1992 now abandoned which is a continuation of 07/827,543 Jan. 29, 1992 now abandoned which is a continuation of 07/618,012 Nov. 26, 1990 now abandoned which is a continuation of 07/489,767 Feb. 26, 1990 now abandoned which is a continuation of 07/358,539 May 30, 1989 now abandoned which is a continuation of 07/075,020 Jul. 16, 1987 now abandoned.

FIELD OF THE INVENTION

This invention relates to protective, absorbent liners for undergarments, especially those that provide their own means for disposal.

BACKGROUND OF THE INVENTION

Conventional sanitary napkins generally comprise an absorbent core having a liquid pervious layer on the body facing side and a liquid impervious layer on the undergarment facing side. Typically, these napkins comprise non-woven fabrics and/or plastic film components which are not readily dispersed in water so that the soiled napkin cannot be disposed of merely by flushing away in a water closet. Accordingly, napkin users are faced with the task of disposing of used napkins in open waste paper baskets, and often resort to wrapping the soiled napkin in tissue before discarding.

Prior art attempts to provide for the disposal of soiled napkins have not, in the main, proved to be entirely successful. Self-contained bags affixed to the garment facing side of the napkin have been employed by manufacturers, but these can interfere with the adhesive attachment sites and are associated with increased material and manufacturing costs. See U.S. Pat. No. 4,182,336. Other approaches have included the use of adhesive means disposed on the sealed ends of the napkin, whereby when the napkin is rolled onto its body-facing side to form a cylinder, the adhesive means are employed to seal the napkin. See U.S. Pat. No. 3,626,945. This later approach has met with little success since the user usually must touch the soiled body-facing side of the napkin when it is being rolled. Moreover, the rolling action can compress the absorbent material and express the absorbed fluids from the exposed sides of the napkin. Another solution to the disposal solution is addressed in Baum, U.S. Pat. No. 4,402,689, which provides a baffle or fluid impermeable surface that may be folded over the body-facing side of the napkin where it is adhesively attached. Although this product provides for disposing the napkin without the user having to touch the soiled napkin surface, the napkin remains in a fully extended position and may not be discreetly deposited into a waste basket.

In a more recent patent by Mattingly, U.S. Pat. No. 4,608,047, a napkin is disclosed which may be folded about two transverse fold lines for disposing. Mattingly describes a newer generation napkin which provides side flaps for overlying the outer crotch portion of an undergarment. The flaps of Mattingly are not designed to be merely an impervious backing material, but are preferably body fluid absorbing. Because of the absorbing nature of these flaps, they may contain body fluid and, accordingly, can complicate the handling and disposal of the napkin. Moreover, because Mattingly is limited to only one securing means and requires that the napkin be folded into three segments prior to being wrapped within the flap portions, napkin users may find this disposal solution to be inconvenient.

Accordingly, there is a need for a sanitary napkin comprising its own convenient disposal means which can be manufactured without significant additional cost. There is also a need for a napkin that can be sealed for disposal and folded into a compact size without leaking.

SUMMARY OF THE INVENTION

A novel sanitary napkin is provided which is capable of being folded and self-sealed for disposal. This napkin includes a backing layer having at least one flap which extends transversely from the longitudinal edge at one end of the napkin. Upon folding the napkin for disposal, the flap of the backing layer is wrapped around the folded portion of the napkin to engage appropriately positioned adhesive means on the other end of the backing layer to effectively enclose the soiled portions of the napkin and keep the absorbed body fluid from leaking. The napkin is designed so that it can be folded onto its body-facing surface about a transverse axis to provide a compact size prior to disposal. The cost of this additional feature is minimal since only a small piece of additional impervious backing layer material is required. Accordingly, a novel napkin is provided which comprises its own convenient, compact disposal means.

In the preferred embodiment of this invention, two flaps are provided extending from opposing longitudinal edges at one end of the napkin. The flaps are conveniently folded back over and detachably secured to the undergarment facing side of the backing layer during use. Each of these folded over flaps has pressure sensitive adhesive means on its exposed surface which contact the undergarment during use. The adhesive means also secure the flaps to the undergarment facing portion of the backing layer once the napkin is folded upon its body-facing side and the flaps are wrapped around the folded portion of the napkin prior to disposal. Pressure sensitive adhesive means are also provided on the other end of the backing layer away from said flaps for adhering the backing layer to the undergarment during use, and for adhering to the flaps when the napkin is folded and the flaps are wrapped around for disposal. Accordingly, in this embodiment each adhesive means serves a dual purpose of adhering a portion of the backing layer to the undergarment during use, and adhering appropriate portions of the backing layer to each other during disposal. In a preferred embodiment, the adhesive means on the flaps and the adhesive means on the other end of the backing layer are positioned so that they contact one another for maximum security of attachment when the flaps are wrapped around the folded napkin.

The present invention also provides a novel method for disposing of a sanitary napkin comprising the steps of rolling or folding and sealing the napkin using one or more self-contained transverse flaps extending from one end of the backing layer. In accordance with this method, the body facing side of the napkin is folded upon itself along a transverse axis and the transverse flap or flaps are unfolded from their position of use against the backing layer and wrapped around the folded portion of the napkin and adhered to undergarment facing portions of the backing layer on the other end of the napkin. In accordance with this method, adhesive means provided on each flap and on the other end of the backing layer are used to adhere the flaps and the backing layer to the undergarment during use, and to each other when the napkin is folded for disposal.

It is, therefore, an object of this invention to provide a sanitary napkin having its own disposal means which can be manufactured without significant additional cost.

It is another object of this invention to provide adhesive means on a sanitary napkin which serve the dual purpose of providing a means for attachment of the napkin to an undergarment and a means for securing the napkin in a folded configuration for disposal.

With these and other object in view, which will become apparent to one skilled in the art as the description proceeds, this invention resides in the novel construction, combination, arrangement of parts and methods substantially as hereinafter described and more particularly defined by the attached claims.

BRIEF DESCRIPTION OF THE DRAWINGS

The accompanying drawings illustrate a complete embodiment of the invention according to the best mode so far devised for the practical application of the principles thereof, and in which.

DETAILED DESCRIPTION OF THE INVENTION

Figure 1:
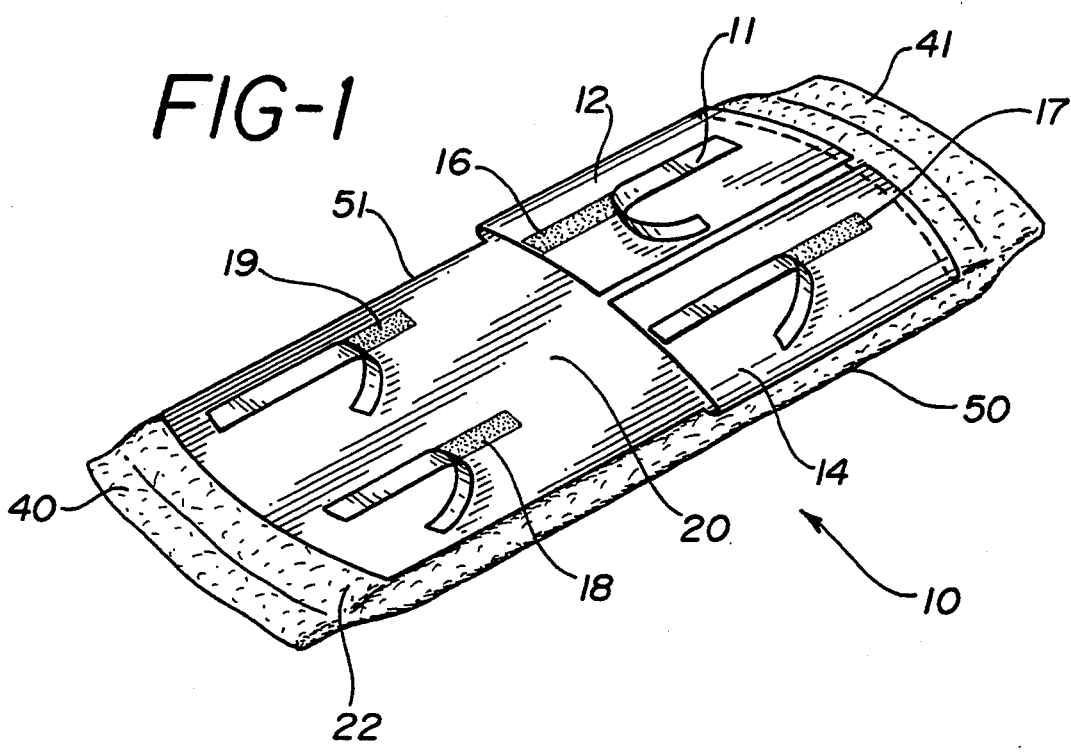
FIG. 1: is a perspective view from the garment-facing side of the napkin illustrating a preferred embodiment with two flaps and four adhesive means with their protective release papers being partially removed.
Figure 2:
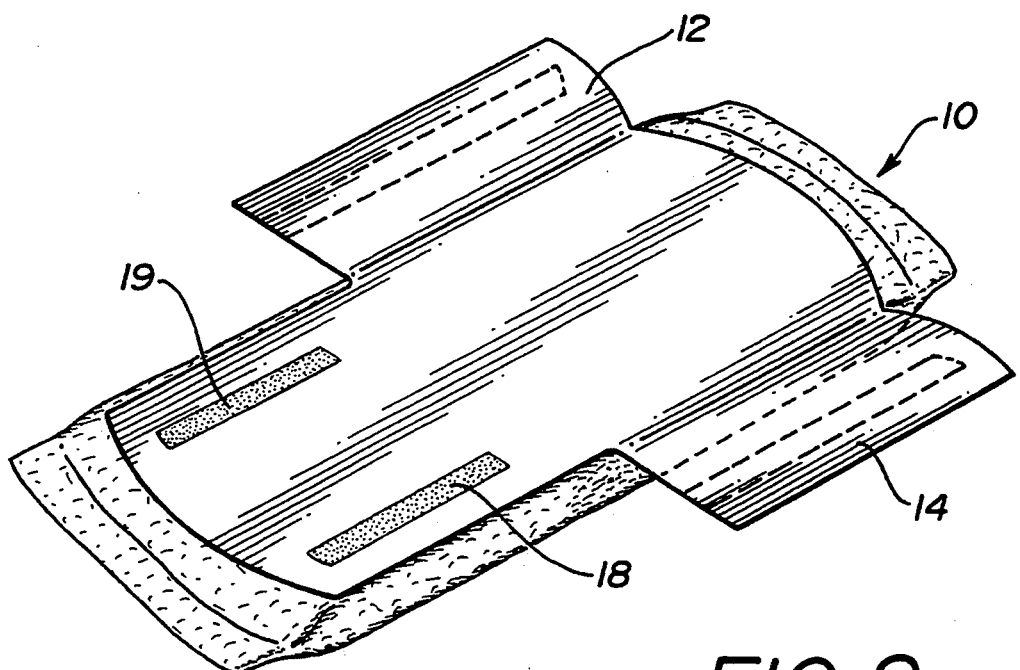
FIG. 2: is a perspective view of the napkin in FIG. 1 illustrating how the flaps may be extended transversely.
Figure 3:
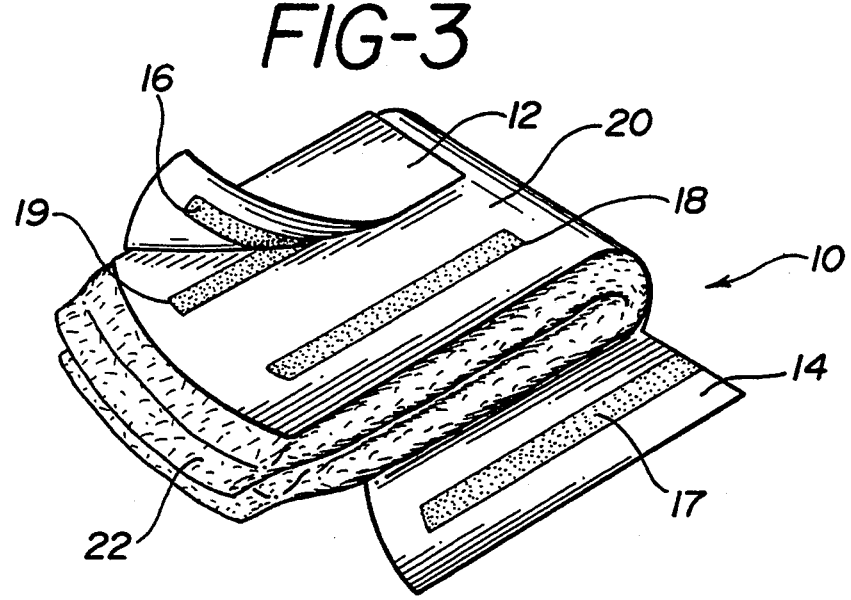
FIG. 3: is a perspective view of the napkin after it has been folded onto its body-facing side illustrating how the flaps may be folded around the napkin and how the adhesive means may be adhered to seal the napkin.

With reference to the drawings, and particularly FIGS. 1-3 thereof, there is shown a preferred sanitary napkin 10 having a body-facing side and an undergarment-facing side. The napkin 10 comprises an elongated central absorbent 22 having two ends 40 and 41, two longitudinal edges 50 and 51, an undergarment-facing side and a body-facing side. Provided on the undergarment-facing side of the absorbent 22 is a backing layer 20, preferably a body-fluid impervious layer. The backing layer 20 is provided with a first adhesive means, depicted as a pair of adhesive strips 18 and 19, which ideally are disposed on the undergarment facing side of the backing layer 20. Extending transversely from one "end" of the backing layer 20 is at least one flap which is adapted to be folded over backing layer 20 and which preferably has its own pressure-sensitive adhesive means on the exposed surface when folded. For the purpose of describing the backing layer 20, the term "end" refers to that portion of said layer defined by a transverse section line taken at about the midpoint of the backing layer's longitudinal side. In a more preferred embodiment of this invention, a sanitary napkin 10 comprises at least two flaps, shown in FIG. 1 as flaps 12 and 14. These flaps extend transversely from the opposing longitudinal edge over the full length of one end of the backing layer 20, and each flap has its own pressure-sensitive adhesive means 16 and 17 on the exposed surface when said flaps are folded over backing layer 20.

In both the above embodiments, the flap or flaps are preferably of sufficient transverse length to overlap a folded portion of said napkin 10 after the napkin has been folded about a transverse axis for disposal. In the one-flap embodiment, the transverse length should be greater than in the two-flap embodiment to provide enough material to overlap the folded portion of said napkin 10, and is preferably substantially equal to the width of the napkin. In the two-flap embodiment of FIG. 3, it is preferred that the flaps have a transverse length of about one half the width of the napkin, although this is not a requirement, and this dimension can vary depending on the location of the adhesive means and the degree of overlap required.

In the preferred embodiment of the present invention, the flap or flaps have a longitudinal length approximately equal to one half the length of the napkins, and the napkin is folded in half about a transverse axis at the midpoint of the napkin for sealing and disposal. It will be appreciated that the napkin can be folded in thirds for disposal, in which case the flap or flaps are required to have a longitudinal length equal to about one third the length of the napkin, and a transverse length sufficient to overlap the triple thickness of the folded napkin. In a yet further embodiment, the napkin may be rolled for disposal, in which case the flap or flaps extending from the end of the napkin are required to have a transverse length sufficient to overlap the rolled napkin, while the longitudinal length may be minimal; i.e., only sufficient to secure the napkin in its rolled configuration.

The adhesive means on the flaps and on backing layer 20 is preferably arranged so that when the napkin 10 is folded about a transverse axis as illustrated in FIG. 3, the first adhesive means on the backing layer, shown as adhesive strips 18 and 19, contacts the adhesive means on the flaps, shown in FIG. 3 as adhesive strip 16 and 17. It is also anticipated that, in either the one-flap or two-flap embodiment of this invention, when the flap or flaps are in the folded position on the garment-facing side of the napkin, they are removably secured to the body-fluid backing layer prior to use. Preferably, the flap or flaps are ultra-sonically or adhesively secured to the backing layer so that they remain in a folded position during attachment but can easily be separated from the backing layer when the napkin is folded for disposal.

The preferred method of this invention initially provides an elongated central absorbent 22 having two transverse ends 40 and 41, two longitudinal edges 50 and 51, an undergarment-facing side and a body-facing side. The central absorbent 22 is covered by a backing layer or body-fluid impervious layer 20 on the undergarment-facing side of the napkin. Backing layer 20 preferably is selected to include at least one flap extending transversely from an end of said layer with means disposed thereon to adhere at least said flap to said backing layer 20. First pressure-sensitive adhesive means are disposed on an undergarment facing side of the backing layer 20 and on the exposed surface of said flap when said flap is adhered to said backing layer. The method proceeds to fold a portion of napkin 10 about a transverse axis onto its body-facing side. The flap or flaps are then released from the backing layer, wrapped around the folded portion of the napkin, and secured to the other side of said backing layer 20 using said first pressure-sensitive adhesive means, thereby sealing the napkin 10 for disposal.

In a most preferred method of this invention, the backing or body-fluid impervious layer 20 is selected to comprise at least two flaps 12 and 14 extending transversely from opposing longitudinal edge of the barrier layer at one end of the napkin. Each of these flaps is selected to have pressure-sensitive adhesive means 16 and 17 on the exposed surface when said flaps are folded over backing layer 20.

The choice of materials for use in the napkin 10 of this invention may be any of the well-known absorbent, super-absorbent, woven and non-woven materials and adhesives utilized in the art of manufacturing these products. The absorbent element 22 of this invention should be made of soft, comfortable material. Adequate absorbency may be built into the core 32 of the absorbent without adding bulk by adding super-absorbent materials, now known, which have the properties of high-liquid retention, e.g. cross-linked acrylate polymers. In a preferred embodiment of this invention, the absorbent element 22 contains conventional resilient materials, e.g., staple-length synthetic fibers, for maintaining the bulk and absorbent capacity of the napkin. Generally, the absorbent element 22 should be about 4–10 inches in length, preferably about 6–9 inches, and is folded approximately in half at the time of disposal.

Figure 5:
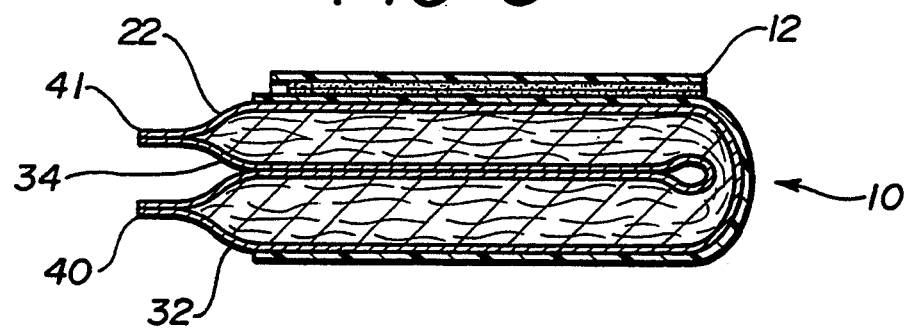
FIG. 5: is a cross-sectional view of the napkin of FIG. 4, taken on the line 4—4 thereof.

As described in FIG. 5, the absorbent element 22 comprises a core 32 which preferably is made of loosely associated absorbent hydrophilic material such as cellulose fibers, wood pulp, regenerated cellulose or cotton fibers, and/or other materials generally known in the art. Such fibers may be chemically or physically modified and the core may include such fibers in combination with other materials, both natural and synthetic such as hydrophilic foams, hydrophilic polymers or the like. For the preferred embodiment of this invention, wood pulp is the material of the choice because of its availability and inexpensive cost.

As is customary in the art, the side of the napkin to be worn against the body of the user is covered with a body fluid pervious layer 34. This surface may be any liquid pervious woven or non-woven material or perforated plastic film. Preferably, body facing material should be a material which readily allows the passage of fluid while retaining little or no fluid in its structure to provide a relatively dry surface next to the skin. Generally, the fluid permeable surface 34 is a single, rectangular sheet of material having a width sufficient to cover the body-facing side of the absorbing element 22.

The body-fluid impervious backing layer 20 is preferably made from fluid impermeable material such as polyethylene or a non-woven material coated with an impermeable film. The impervious layer should preferably allow the passage of air and moisture vapor while substantially blocking the passage of liquids. The impervious layer 20 in the preferred embodiment is sealed together with the body facing layer 34 around the perimeter of the absorbent element 22 to prevent leakage of fluid from the sides of the absorbent element 22. The impervious layer 20 may be heat sealed or fastened by way of adhesives to the core 32 or to the core 32 wrapped in a pervious layer cover 34. The fluid impervious layer 20 is generally fastened to the core 32 by means of a plurality of longitudinally extending lines of adhesive. Preferably, however, the impervious layer 20 is heat bondable material such as polyethylene, which may be bonded to the pervious layer 34 to completely enclose the core 32.

Figure 4:
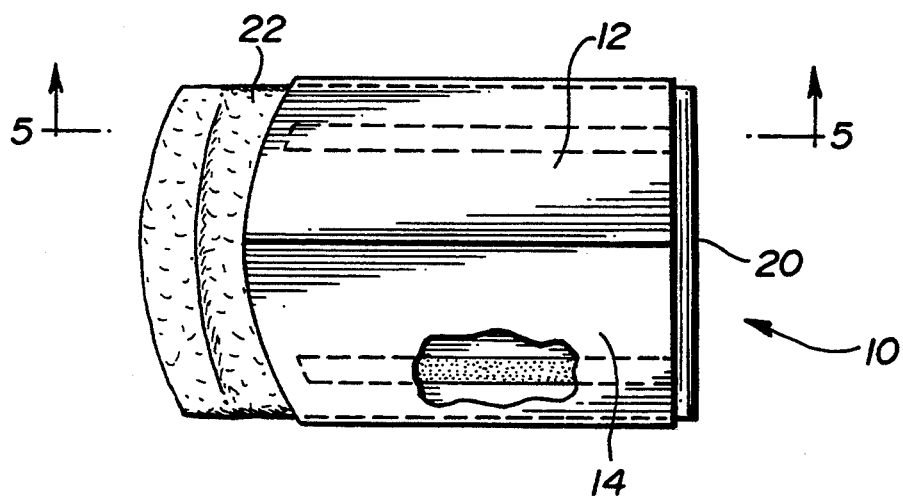
FIG. 4: is a top planar view of a fully sealed napkin which is shown partially cut away to illustrate how the adhesive means have been adhered to seal the flaps.

In the preferred embodiment of this invention, the impervious layer 20 is provided with at least one integral flap extending transversely from a longitudinal edge at one end thereof which may be overlapped around the napkin after it has been folded onto its body-facing surface to seal the napkin for disposal. In a particularly preferred embodiment of this invention, the impervious layer 20 comprises at least two flaps and which extend transversely from opposing edges at one longitudinal end of the napkin 10. Ideally each of these flaps has its own adhesive means which serve as a means for attaching the napkin to an undergarment and also as a means for adhering the flaps to the impervious layer after the napkin is folded for disposal. As shown in FIG. 4, the adhesive means on the flaps and backing layer of the more preferred embodiment are arranged so that they overlap one another when the flaps and are folded around the napkin. In this embodiment, adhesive means 16 on flap 12 is aligned with adhesive means 19 on backing layer 20 and adhesive means 17 on flap 14 is aligned with adhesive means 18 on backing layer 20 to secure the flaps 12 and 14 in the position for napkin disposal as depicted in FIGS. 3 and 4. In an alternate embodiment, the flap or flaps are not integral with the backing layer but are obtained by securing a separate piece of material, preferably a liquid impervious material, to the backing layer so that the ends of the material extend transversely beyond the longitudinal edges of the backing material.

The adhesive materials used for the sanitary napkin of this invention should be made of any known pressure-sensitive adhesive materials suited for the purposes of this invention. Compositions suitable for sanitary napkins include, for example, the water-based, pressure-sensitive adhesives such as the acrylate adhesives, e.g., vinyl acetate-2 ethyl hexyl acetate copolymer which is generally combined with tackifiers such as, for example, ethylene amine. Alternatively, the adhesive may comprise the rapid setting thermoplastic hot-melt adhesives. The adhesive elements may also comprise a two-sided adhesive tape or materials based on an elastomer selected from natural or synthetic rubbers. In the illustrated preferred embodiment of this invention, four adhesive means 16, 17, 18, and 19 are utilized for the dual purpose of securing the napkin to the undergarment during use and for adhering the flaps 12 and 14 to the impervious layer 20 after the napkin 10 has been folded for disposal. As is customary in the art of sanitary napkins, the adhesive means are covered by a release paper material, i.e., strip 11 in FIG. 1, which protects the adhesive surface until the napkin is ready for attachment to the undergarment.

The release paper means of this invention may be made of any sheet-like material which adheres with sufficient tenacity to the adhesive means 16, 17, 18 and 19 to remain in place, but which can be readily removed when the napkin 10 is to be used. Conventional materials used for this purpose include woven webs, non-woven bonded fiber webs, non-woven threaded webs, threaded reinforced non-woven webs, plastic films, and/or laminates of the above. A particularly useful material for release paper is a semi-bleached kraft paper, the adhesive contacting side of which has been silicone-coated to provide easier removal from the adhesive means.

From the foregoing, it can be realized that this invention provides an improved sanitary napkin with its own convenient disposal means. The napkin can be manufactured inexpensively and only requires a small piece of additional impervious material to form the flap or flaps on its garment facing side. Accordingly, this invention provides a cleaner and more discreet way of sealing the napkin for disposal and satisfies a need which has, heretofore not been addressed by prior art products. Although various embodiments have been illustrated, this was for the purpose of describing, but not limiting the invention. Various modifications, which will become apparent to one skilled in the art, are within the scope of this invention described in the attached claims.

I claim:

1. A sanitary napkin capable of being folded or rolled and self-sealed for disposal comprising:
    (a) an elongated central absorbent element having two ends, two longitudinal edges, an undergarment facing side and a body-facing side;
    (b) a backing layer substantially covering said undergarment-facing side of said absorbent element,
    (c) one or two flaps extending transversely beyond the longitudinal edge of said backing layer at one end thereof, and
    (d) first adhesive means disposed on said backing layer in a position to adhere said flap to said backing layer when said napkin is rolled or folded for disposal about transverse axis and said flap is wrapped around said rolled or folded napkin.

2. The sanitary napkin of claim 1 wherein said backing layer comprises a liquid impervious layer.

3. The sanitary napkins of claim 1 wherein said flap is an integral part of said backing layer.

4. The sanitary napkin of claim 1 wherein said first adhesive means is disposed on the undergarment facing side of said backing layer.

5. The sanitary napkin of claim 1 wherein said flap is folded over and detachably secured to said backing layer.

6. The sanitary napkin of claim 5 wherein pressure-sensitive adhesive means are disposed on the exposed surface of said folded over flap.

7. The sanitary napkin of claim 1 wherein said flap has a transverse length approximately equal to the width of said napkin.

8. The sanitary napkin of claim 6 wherein said adhesive means on said flap is arranged to adhere to said first adhesive means on said backing layer when said flap is wrapped around said rolled or folded napkin.

9. The sanitary napkin of claim 1 wherein two flaps extend transversely beyond opposing longitudinal edges of said backing layer at one end thereof.

10. The sanitary napkin of claim 9 wherein said flaps have a transverse length of about one half the width of said napkin.

11. The sanitary napkin of claim 9 wherein said flaps are of sufficient transverse length to overlap said rolled or folded portion of said napkin.

12. The sanitary napkin of claim 9 wherein said flaps are folded over and detachably secured to said backing layer.

13. The sanitary napkin of claim 12 wherein pressure sensitive adhesive means are disposed on the exposed surfaces of said folded-over flaps.

14. The sanitary napkin of claim 13 wherein said adhesive means on said flaps are arranged to adhere to said first adhesive means on said backing layer when said flaps are wrapped around said folded napkin.

15. A method of self-sealing a sanitary napkin for disposal comprising:
    (a) providing an elongated central absorbent having two ends, two longitudinal edges, an undergarment-facing side and a body-facing side, and having a backing layer on said undergarment-facing side with one or two flaps extending transversely beyond a longitudinal edge of said backing layer thereof, said backing layer having first pressure-sensitive adhesive means disposed thereon.
    (b) rolling or folding said napkin about a transverse axis;
    (c) wrapping said flap around said rolled or folded portion of said napkin;
    (d) adhering said flap to said backing layer using said first pressure-sensitive adhesive means, thereby sealing said sanitary napkin for disposal.

16. The method of claim 15 wherein said first adhesive means is disposed on the undergarment facing side of said backing layer at the other end thereof.

17. The method of claim 15 wherein said flap is folded over said one end of said backing layer and detachably secured thereto prior to use.

18. The method of claim 17 wherein said flap includes pressure-sensitive adhesive means on the exposed surface of said folded over flap.

19. The method of claim 18 wherein said pressure-sensitive adhesive means on said flap is arranged to adhere to said first adhesive means on said backing layer when said flap is wrapped around said rolled or folded napkin.

20. The method of claim 15 wherein said backing layer is selected to comprise at least two flaps extending transversely from opposing longitudinal edge at said one end of said backing layer.

21. The method of claim 20, wherein each of said flaps is selected to have a sufficient transverse length to overlap said napkin after said napkin has been rolled or folded about a transverse axis.

22. The method of claim 21, wherein each of said flaps are adhered to said first adhesive means on said backing layer when said flaps are wrapped around said rolled or folded napkin.

23. A sanitary napkin capable of being folded or rolled and self-sealed for disposal comprising:
    (a) an elongated central absorbent element having two ends, two longitudinal edges, an undergarment facing side and a body-facing side;
    (b) a backing layer substantially covering said undergarment-facing side of said absorbent element;
    (c) at least one flap extending transversely beyond the longitudinal edge of said backing layer at one end thereof; and
    (d) first adhesive means disposed on the undergarment-facing side of said backing layer in a position to adhere said flap to said backing layer when said napkin is rolled or folded for disposal about a transverse axis and said flap is wrapped around said rolled or folded napkin.

* * * * *